(12) United States Patent
Cahill et al.

(10) Patent No.: US 6,635,152 B1
(45) Date of Patent: Oct. 21, 2003

(54) PROCESS OF DRIVING A NON-POLYMERIZATION SOLUTION-PHASE PHOTOCHEMICAL TRANSFORMATION

(75) Inventors: Paul A. Cahill, Dayton, OH (US); Richard N. Steppel, Dayton, OH (US)

(73) Assignee: Exciton, Inc., Dayton, OH (US)

( * ) Notice: Subject to any disclaimer, the term of this patent is extended or adjusted under 35 U.S.C. 154(b) by 0 days.

(21) Appl. No.: 09/589,908

(22) Filed: Jun. 7, 2000

(51) Int. Cl.[7] ............................... C07C 6/00; C07F 1/00
(52) U.S. Cl. ................................ 204/157.15; 204/157.6
(58) Field of Search .......................... 204/157.15, 157.6

(56) References Cited

U.S. PATENT DOCUMENTS

| | | | | |
|---|---|---|---|---|
| 4,929,869 A | * | 5/1990 | Yonezawa et al. | 313/639 |
| 5,076,813 A | | 12/1991 | Alberici et al. | 44/300 |
| 5,616,882 A | | 4/1997 | Nichols et al. | 102/287 |
| 5,679,115 A | * | 10/1997 | Fritzsche et al. | 8/444 |

OTHER PUBLICATIONS

Naman et al., "Photocatalytic Production of Hydrogen From Hydrogen Sulfide in Ethanolamine Aqueous Solution Containing Semiconductors Dispersion", Energy Environ. Prog. I (1991), vol. D, pp. 13–23. Abstract only. no month avaiable.*

* cited by examiner

*Primary Examiner*—Edna Wong
(74) *Attorney, Agent, or Firm*—Wood, Herron & Evans, L.L.P.

(57) ABSTRACT

The present invention relates to a process for driving a non-polymerization solution-phase photochemical transformation. A sensitizer, such as a substituted diaminobenzophenone having a solubility in norbornadiene greater than that of Michler's Ketone, may be added to norbornadiene to form a solution, wherein the sensitizer decreases the induction period at the beginning of the reaction, increases the photon or quantum efficiency of conversion of norbornadiene to quadricyclane, and increases the rate of conversion at the end of the reaction. If the solution is irradiated with light from a metal halide-doped mercury arc lamp to photochemically transform the norbornadiene to quadricyclane, the conversion is more efficient than when other light sources are utilized. Furthermore, the addition of triethylamine to the solution tends to result in the formation of fewer by-products in the transformation reaction.

8 Claims, 2 Drawing Sheets

PROCESS OF DRIVING A NON-POLYMERIZATION SOLUTION-PHASE PHOTOCHEMICAL TRANSFORMATION

The invention claimed herein to the extent funding by the Government contributed to the development thereof may be manufactured, used, and licensed by or for the Government for governmental purposes without the payment of any royalties thereon.

FIELD OF THE INVENTION

This invention relates to fuels. More specifically, this invention relates to quadricyclane and a highly efficient process for producing quadricyclane.

BACKGROUND OF THE INVENTION

Quadricyclane, or tetracyclo[2.2.1.0$^{2,6}$.0$^{3,5}$]heptane, is known in the prior art as a chemical for energy storage, in particular, solar energy storage. Quadricyclane has also been recognized as a potential fuel for internal combustion engines, as described in U.S. Pat. No. 5,076,813; and as a rocket propellant, as described in U.S. Pat. No. 5,616,882. In such applications, quadricyclane may be used alone or as a component along with other hydrocarbon fuels for the purpose of modifying the fuel characteristics, e.g., increasing the heat of combustion, or fuel density.

Quadricyclane has been identified as a possible high-energy replacement for, or additive to, current hydrocarbon-based rocket propellants. Quadricyclane's highly strained structure gives it a specific impulse and density that is greater than current hydrocarbon-based rocket propellants. It is hoped that replacing current rocket propellants with quadricyclane will enable launching payloads having greater mass on otherwise equivalent launch vehicles.

Currently, the accepted synthesis of quadricyclane is via a photochemical transformation from norbornadiene, bicyclo[2.2.1]hepta-2,5-diene.This transformation may be carried out by direct ultraviolet radiation of purified or unpurified norbornadiene utilizing mercury arc lamps. The transformation may be made more efficient by using a sensitizer molecule that absorbs the ultraviolet light and transfers its energy to the norbornadiene. However, it has been determined that the use of some prior art sensitizers simultaneously leads to a significant decrease in the rate of quadricyclane production with increased conversion. Furthermore, the addition of more sensitizer in an effort to gain better efficiencies in the production rate is not preferable, particularly in continuous flow reactors, because of the additional steps required.

Sensitizers for the transformation of norbornadiene to quadricyclane have been studied for almost 40 years. Benzophenone, 4-dimethylaminobenzophenone, 4,4'-bis (dimethylamino)-benzophenone (Michler's Ketone), as well as various copper salts have been reported to be relatively efficient sensitizers for the reaction. As mentioned previously, ultraviolet light sources to drive the photochemical transformation have included sunlight, simulated sunlight (for solar energy storage applications), and both medium and high-pressure mercury arc lamps.

Notwithstanding the prior efforts and developments in the production of quadricyclane, what is needed is a less expensive and more efficient process for carrying out the solution phase photochemical transformation of converting norbornadiene to quadricyclane.

OBJECTIVES OF THE INVENTION

It has therefore been an object of the present invention to provide a less expensive and more efficient process for carrying out solution-phase photochemical transformations.

It has also been an object of the present invention to provide a less expensive process for converting norbornadiene into quadricyclane.

It has been a further object of the present invention to provide a more efficient process for converting norbornadiene to quadricyclane.

Another object of the present invention is to provide relatively inexpensive quadricyclane manufactured by the process described herein in order to provide a relatively low cost yet high-energy fuel.

SUMMARY OF THE INVENTION

The objects of the present invention are achieved by irradiating a solution of purified or unpurified norbornadiene and a sensitizer having a solubility in norbornadiene greater than that of Michler's Ketone with light emissions from a light source having wavelengths in the range of about 250 nm to about 400 nm and, preferably, in the range of 340 nm to 390 nm. Mercury arc lamps, including both medium and high-pressure arc lamps, in which the lamp is doped with small amounts of other elements enhance the emission of the mercury arc in the near-UV (UVA), region of the spectrum. These doping additives have the ultimate effect of increasing the efficiency of light output at wavelengths useful for photochemical transformations when used both in conjunction with and without the aid of a sensitizer.

In a preferred embodiment, metal halide-doped mercury arc lamps and, specifically, iron halide-doped mercury arc lamps, that have enhanced outputs in the range of about 340 nm to about 390 nm are used to enhance the sensitized conversion of the norbornadiene to quadricyclane. The enhanced emission wavelength of an iron halide-doped mercury arc lamp in the range of about 340 nm to about 390 nm overlaps with the absorption of diaminobenzophenone sensitizers, e.g., Michler's Ketone. It has been found that the use of an iron halide-doped mercury arc lamp provides an increase of about 20% in the conversion rate of norbornadiene to quadricyclane when used with Ethyl Michler's Ketone as the sensitizer, as further discussed below. The photochemical transformation is preferably carried out at a temperature in the range of about −40° C. to about 60° C.

Also in a preferred embodiment, the sensitizer in the conversion of norbornadiene to quadricyclane is Ethyl Michler's Ketone (4,4'-bis(diethylamino)benzophenone). Use of Ethyl Michler's Ketone as the sensitizer has led to a decrease in the induction period at the beginning of the conversion reaction, and an increase in the photon or quantum efficiency of conversion of norbornadiene to quadricyclane.

The result of replacing Michler's Ketone with Ethyl Michler's Ketone reduces or eliminates the requirement of using purified norbornadiene to obtain the highest conversion rates to quadricyclane. The use of Ethyl Michler's Ketone improves the conversion rate of norbornadiene to quadricyclane by about 40% when compared with the use of Michler's Ketone as a sensitizer. Also, the addition of triethylamine to the reactor reduces the amount of side products formed during the transformation, thereby reducing downtime.

Because there is no significant increase in cost to drive the photochemical transformation by using an iron halide-doped mercury arc lamp and/or Ethyl Michler's Ketone and/or triethylamine, it is significantly less expensive to produce quadricyclane by the present inventive process. Thus, with the present inventive process it is more efficient and less expensive to produce quadricyclane, ultimately potentially allowing lower cost access to outer space.

DETAILED DESCRIPTION OF THE PREFERRED EMBODIMENT

Figure 1:
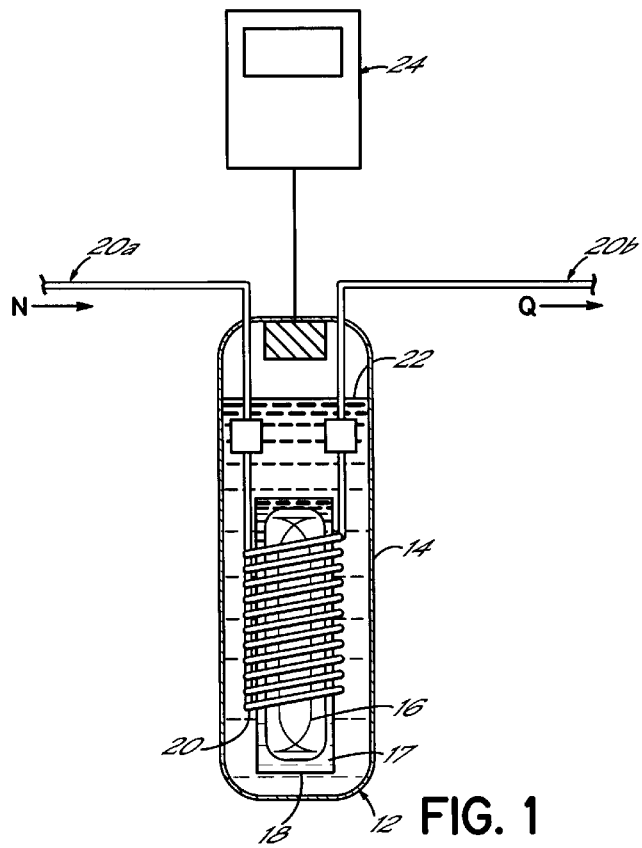
FIG. 1 shows a schematic representation of a continuous flow reactor useful in the present inventive process of converting norbornadiene to quadricyclane.

In the present inventive process for production of quadricyclane, a sensitizer is added to norbornadiene to form a solution. "Quadricyclane", as will be understood herein, includes all substituted quadricyclanes and heteroquadricyclanes. "Norborhadiene", as will be understood herein, includes all substituted norbornadienes and heteronorbornadienes. The sensitizer used in the preferred process has a solubility in norbornadiene greater than that of Michler's Ketone (MK) under the same conditions. In the most preferred process, the sensitizer is Ethyl Michler's Ketone (EMK); however, any substituted diaminobenzophenone having a solubility in norbornadiene greater than that of MK may be used. Other suitable sensitizers include, for example:
4,4'-bis(dipropylamino)benzophenone;
4,4'-bis(dibutylamino)benzophenone;
4,4'-bis(methylethylamino)benzophenone; and
4,4'-bis(t-butyl-methylamino)benzophenone.

The solubility of MK in norbornadiene does not appreciably exceed 0.32% by weight at room temperature, whereas the solubility of EMK in norbornadiene is at least 3.86% by weight at room temperature. When the solution of norbornadiene and EMK is irradiated, the photochemical transformation is driven by the wavelengths of ultraviolet light, preferably in the range of about 250 nm to about 400 nm. The EMK sensitizer absorbs the ultraviolet light and transfers the absorbed energy to the norbornadiene, whereby quadricyclane is produced by photochemical conversion generally expressed as:

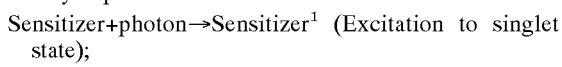

Sensitizer+photon→Sensitizer$^1$ (Excitation to singlet state);

Sensitizer$^1$→Sensitizer$^3$ (Intersystem crossing to the triplet state); and

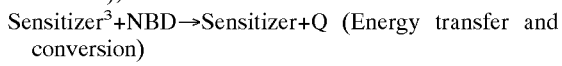

Sensitizer$^3$+NBD→Sensitizer+Q (Energy transfer and conversion)

The rates of conversion of norbornadiene to quadricyclane over a wide range of conversion, for example, 10%–60% with MK and 10%–80% or higher with EMK, is linear in time for both sensitizers at all concentrations, for example, about 0.2 to about 3.86% and with all light sources, for example, 400 W and 1300 W mercury arc lamps and a 400 W iron halide-doped mercury arc lamp, and irradiation times of short and long duration. The total number of photons appear to be the determining factor in the rate of conversion. This suggests that the reaction proceeds with a constant quantum yield of conversion from norbornadiene to quadricyclane over a wide range of concentrations of norbornadiene and that the quantum yield decreases somewhat at high conversions. The quantum yield of reversion of quadricyclane to norbornadiene appears to be very low because the photostationary state consists of at least 99.5% quadricyclane.

Use of EMK as the sensitizer in the photochemical transformation of norbornadiene to quadricyclane decreases the induction period at the beginning of the reaction, increases the photon or quantum efficiency of conversion of norbornadiene to quadricyclane, and increases the rate of conversion at the end of the reaction. As discussed further in Example 1 below, in parallel experiments, improvements of close to 40% in the conversion rate of norbornadiene to quadricyclane are obtained when using EMK as the sensitizer rather than MK, with all other conditions being the same. Use of EMK rather than MK reduces or eliminates the requirement of purifying norbornadiene to obtain the highest conversion rates of norbornadiene to quadricyclane.

In a second preferred embodiment of the present inventive process, the photochemical transformation is driven by a metal halide-doped mercury arc lamp. Most preferably an iron halide-doped mercury arc lamp is used that has enhanced radiation output of about 340 to about 390 nm. This emission wavelength overlaps with the absorption wavelength of substituted diaminobenzophenones such as MK and EMK. As discussed further below, in Example 2, an increased conversion of norbornadiene to quadricyclane of about 22% was achieved using iron halide-doped mercury arc lamps instead of a traditional mercury arc lamp, with all other conditions being the same. The halide used in the iron halide-doped mercury arc lamp need not be limited to any specific halide.

Preferably, the emission wavelength for the photochemical transformation is filtered to remove wavelengths shorter than about 300 nm. Filtration is preferably accomplished by use of an external irradiator type photoreactor such as available from Electro-Lite Corp., Danbury, Conn., in which light from the metal halide-doped mercury arc lamp is directed at least partially through vapors of the reactor mixture and onto a freed reaction mixture surface. In such cases, the shorter wavelengths may be absorbed by norbornadiene vapor, or by liquid on the container internal surfaces, and subsequently deposit absorbing and scattering by-products on the flask or the window of a reaction vessel. Removal of the short wavelengths can be accomplished with borosilicate glass or other suitable materials. Preferably it is accomplished with the use of a pyrex vessel.

Preferably, the photochemical transformation is carried out at a temperature in the range of about −40° C. to about 60° C. That is, the photochemical transformation is carried out above the melting temperature of the mixture of norbornadiene and quadricyclane. Norbornadiene melts at −11° C. and quadricyclane melts at −40° C., the mixture of the two having a melting point lower than each substance alone. The photochemical transformation is carried out more preferably in a temperature range of about −10° C. to about 30° C. and most preferably at about 0° C. The temperature of the photochemical transformation minimizes by-product contamination of the reactor in which the photochemical transformation takes place, as discussed more fully below.

In another preferred embodiment of the present inventive process, the addition of a small amount of a base, generally an amine, and more specifically a trialkylamine, such as triethylamine or an aromatic amine such as pyridine, either soluble in the sensitizer/norbornadiene solution or rendered insoluble through linkage to a polymer as in cross-linked polystyrene co-vinylpyridine, greatly decreases the amount of undesirable by-products, more specifically, polymeric side products, formed in the reaction chamber during the photochemical transformation. Polymeric materials that are deposited onto the sides of the reaction chamber may lead to decreased conversion efficiencies and to increased reaction chamber clean-up times. Preferably, an addition in the range of about 0.1 to about 1% by volume of triethylamine to norbornadiene only slightly affects conversion rates and yet leads to reduced amounts of polymeric side products formed during the transformation.

As seen in FIG. 1, a schematic drawing of a preferred embodiment of the reactor 12 for carrying out the present inventive process is shown. In accord with the present inventive process, a continuous flow reactor 12 has a light shield 14 enclosing a lamp 16 contained within a well 18. A spiral tube 20 having an inlet 20a and an outlet 20b is axially aligned around the lamp 16. The light shield 14 contains coolant fluid 22 in order to cool the spiral tube 20. A second coolant fluid 17 flows within the well 18 to cool the lamp 16. The coolant fluids 17,22 are any suitable coolants known in the art, for example, water or antifreeze solutions. In the preferred process, a solution of norbornadiene and a sensitizer, indicated by directional arrow N, is pumped through the spiral tube inlet 20a, the solution then circulates around the lamp 16 where it is irradiated and, thereby, converted to quadricyclane indicated by directional arrow Q, which is then pumped out of the reactor via tube outlet 20b. Use of a continuous flow reactor 12 produces a lighter color product than does a batch reactor (not shown), because purer quadricyclane is produced.

A radiometer 24 is used to monitor and potentially correct the out put of lamp 16. The radiometer 24 is International Light model 1400A equipped with a waterproof SEL 033/B/W detector and an OD2 neutral density filter available from International Light, Newburgport, Mass.

Any combination of the preferred embodiments of the inventive processes disclosed herein may be used in efficiently converting norbornadiene to quadricyclane. That is, any substituted diaminobenzophenone may be added to norbornadiene to form a solution which is converted to quadricyclane via the inventive process step of irradiating the substituted diaminobenzophenone/norbornadiene solution with an iron halide-doped mercury arc lamp. Preferably the substituted diaminobenzophenone is added to norbornadiene in an amount in the range of about 0.2% to about 3.86% by weight. Alternatively, norbornadiene, in solution with a substituted diaminobenzophenone having a solubility in norbornadiene greater than that of MK, e.g., EMK, is photochemically transformed to quadricyclane via irradiation by use of a high-pressure mercury arc lamp, of a type well known in the art.

Furthermore, an iron halide-doped mercury arc lamp, available from Electro-Lite Corporation, Danbury, Conn., may be used to photochemically transform norbornadiene, in solution with a substituted diaminobenzophenone having a solubility in norbornadiene greater than that of MK, e.g., EMK, into quadricyclane. Moreover, a base, such as triethylamine, may be added to the sensitizer and norbornadiene solution as the process is carried out in either a batch reactor or a continuous flow reactor to reduce the volume of side products formed during the transformation reaction.

The inventive process disclosed herein may be carried out in an immersion well type batch reactor available from Ace Glass Inc., Vineland, N.J., or Hanovia, Union, N.J., which are known in the art, as well as external radiator type batch reactors available from Electro-Lite Corporation, Danbury, Conn., in addition to continuous flow reactors of the type shown in FIG. 1 and described in further detail below in Example 4. Further details of the present invention will now be disclosed in the context of the several examples which follow.

EXAMPLE 1

Irradiation of separate 5 ml aliquots of stirred norbornadiene in solution with Michler's Ketone (MK) or Ethyl Michler's Ketone (EMK), were carried out under nitrogen in 25 ml Pyrex® flasks within an Electro-Lite ELC 4000 curing unit (Electro-Lite Corporation, Danbury, Conn.), equipped with a 400 W iron halide-doped (UVA) lamp at a distance of approximately 25 cm. The norbornadiene used in these experiments was not pre-purified. The conversion to quadricyclane was measured by gas chromatography as a function of time by withdrawing a drop of solution via syringe. The conversion is plotted in FIG. 2. The relative rate of conversion to quadricyclane was 39% greater for the solutions containing Ethyl Michler's Ketone at 3.86% by weight than for the solutions containing Michler's Ketone at 0.32% by weight. Thin layer chromatography indicated that both sensitizers were slowly consumed in these experiments. The reaction was carried out under atmospheric pressure at about 60° C. Norbornadiene to quadricyclane conversion for various concentrations of Ethyl Michler's Ketone and Michler's Ketone under iron halide-doped mercury arc lamp irradiation. Ethyl Michler's Ketone provides greater than 99% conversion to Quadricyclane, a significant improvement over Michler's Ketone.

EXAMPLE 2

The experiment described in Example 1 was repeated with parallel reactions of 0.32% by weight MK and 0.75% by weight EMK each in 5 ml of purified norbornadiene. Norbornadiene is purified for purposes of this experiment by the following process. Silica gel, 2% of the weight of the norbornadiene to be purified, is placed in a flash chromatography column. Norbornadiene is gravity or pressure filtered through the silica gel and stored in tightly closed glass containers. The norbornadiene purified in this manner is noticeably lighter yellow in color than the readily available commercial grade material but still contains small amounts of other components. Commercial norbornadiene contains cycloheptatriene, toluene, dicyclopentadiene and cyclopentadiene+norbornadiene cycloaddition products, a stabilizer, as well as other unidentified components.

After 16 hours of irradiation with a 400 W iron halide-doped mercury arc lamp at a distance of approximately 25 cm, the EMK sample showed a conversion of 65.86% compared to 53.79% for the MK-containing solution, an improvement of 22%. The lamp is of the type available from Electro-Lite Corporation, Danbury, Conn.

Figure 2:
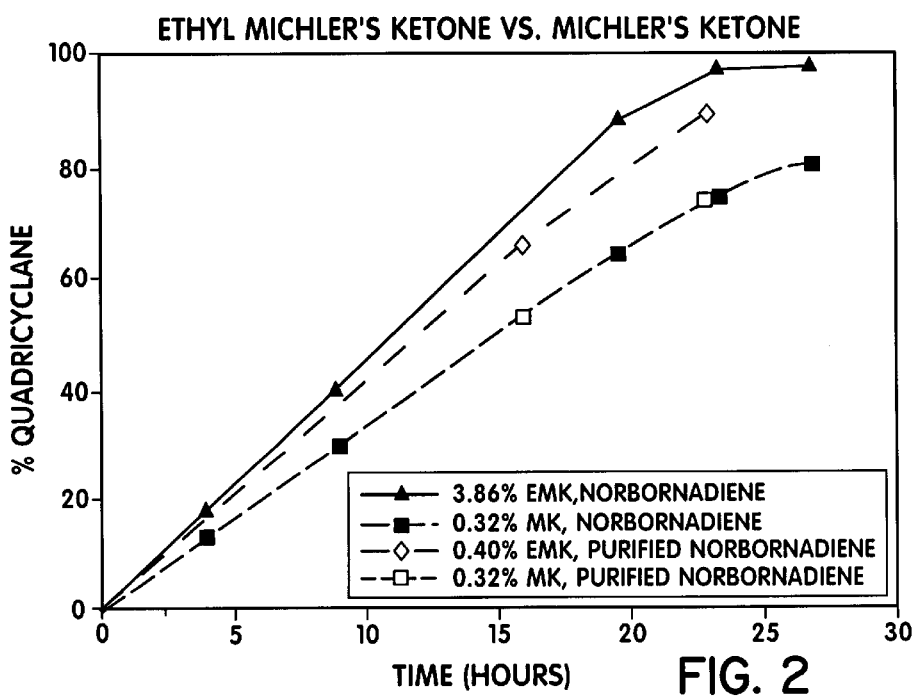
FIG. 2 shows a comparison of the rates of conversion of norbornediene to quadricyclane utilizing Ethyl Michler's Ketone (EMK)

This experiment was also carried out as described in Example 1 with purified norbornadiene containing Michler's Ketone (0.32% by weight, in 5 ml of norbornadiene), and Ethyl Michler's Ketone (0.40% by weight, in 5 ml of norbornadiene). The relative rate of conversion is shown in FIG. 2. The conversion rate is significantly greater with Ethyl Michler's Ketone than with Michler's Ketone.

The experiments as described in Example 2 were carried out at atmospheric pressure at 60° C.

EXAMPLE 3

Irradiations of 1 ml samples of 0.5% Ethyl Michler's Ketone in norbornadiene were carried out with a 400 W high-pressure mercury arc lamp and a 400 W iron halide-doped mercury arc lamp as available from Electro-Lite Corporation, Danbury, Conn. The linear conversion rate was 11.48% per hour for the doped lamp as compared to 9.72% per hour for the undoped lamp. This translates to an improvement in conversion rate of 18% with the iron halide-doped lamp. This transformation was carried out at atmospheric pressure at 60° C.

EXAMPLE 4

The continuous process of converting to quadricyclane was demonstrated with the continuous flow reactor 12 shown in FIG. 1. The apparatus has a Model J06PM22HGC1 1300 W medium pressure mercury arc lamp with a 6.5 inch arc length as available from Jelight Company, Inc., Irvine, Calif., inside a water cooled quartz well that was centered on a spiral tube containing a continuously pumped norbornadiene solution (1.2 mL/min.), of Ethyl Michler's Ketone (0.40% by weight). The norbornadiene was not previously purified. Samples were collected at fixed eight minute intervals. The conversion to quadricyclane was measured by gas chromatography and the results are plotted in FIG. 3. The plot shows a generally linear conversion of norbornadiene to quadricyclane as a function of time throughout most of the process, which lasted 216 minutes. This continuous process was carried out at 25° C.

Plot of conversion vs. sample number for a continuous reactor with a nominal 1300 W medium-pressure mercury arc lamp. For this geometry, the conversion is linear in time between approximately 20% and 90% conversion.

EXAMPLE 5

Figure 4:
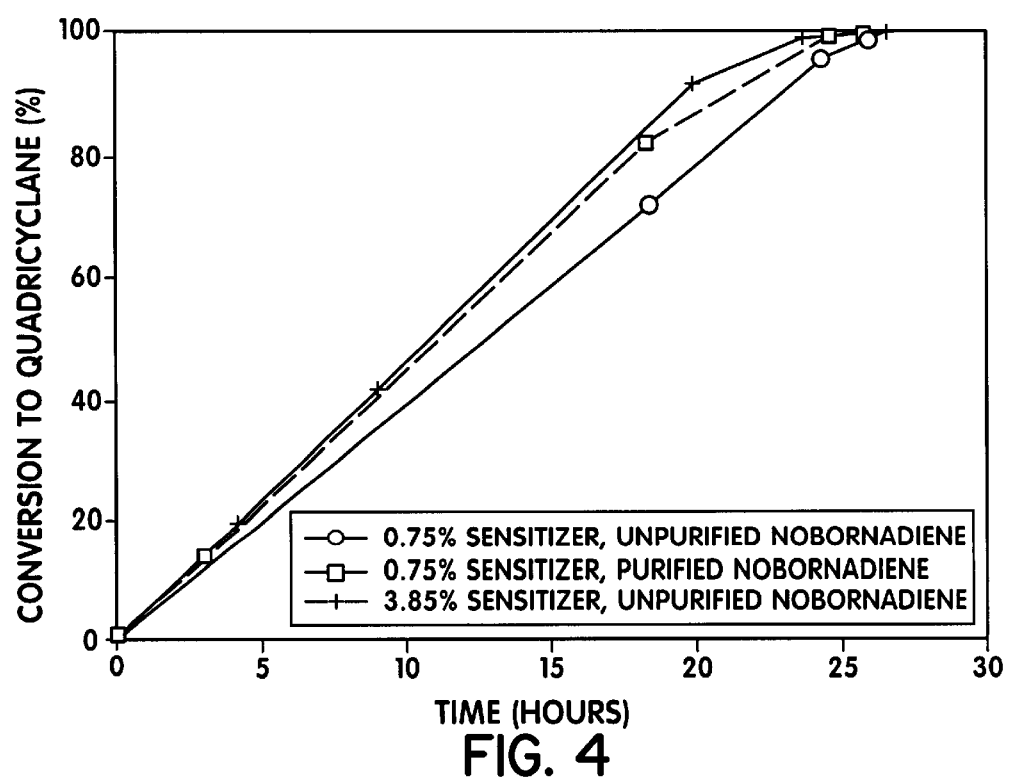
FIG. 4 shows the conversion of norbornediene to quadricyclane with different amounts of a sensitizer.

As can be seen generally in FIG. 4, the high solubility of a sensitizer such as EMK reduces or eliminates the need for purification of the norbornadiene. In parallel experiments in which purified and unpurified samples of norbornadiene were each sensitized with 0.75% by weight EMK and irradiated with a 400 W iron halide-doped mercury arc lamp as available from Electro-Lite Corporation, Danbury, Conn., the conversion rate to quadricyclane was in the range of 15–25% greater in the case of purified norbornadiene. In similar experiments in which unpurified norbornadiene sensitized with 3.85% by weight EMK, and purified norbornadiene sensitized with 0.75% by weight EMK were irradiated in parallel, increases relative to unpurified, 0.75% by weight EMK sensitized mixtures, were both in the range of 15–25%. Therefore, the greater amounts of the relatively high solubility EMK sensitizer can be used in place of norbornadiene purification for more efficient quadricyclane production.

The improvements from replacing MK with EMK may be related to the increased solubility of EMK to that of MK in norbornadiene. For example, the improved performance may be due to increased relative absorption by the sensitizer over that of impurities present or formed during the conversion. However, the improved performance may also result indirectly from a decrease in self-quenching that may occur near the solubility limit in MK. The exact mechanisms of this improvement are unknown, difficult to test, and were not predicted prior to testing.

Ethyl Michler's Ketone was utilized initially to solve the problem of incomplete conversion of norbornadiene to quadricyclane observed when using MK. Multiple additions of MK during the transformation were required to reach high conversions using commercially available norbornadiene, and it was first thought that an initial higher quantity of EMK would give only an equivalent rate of reaction with high conversion and no additional benefit. Unexpectedly, in addition to higher conversion, the efficiency of EMK as a sensitizer has been found to be higher than that of MK.

As a further consequence of this unexpected finding, it is contemplated that EMK, or any other diaminobenzophenone sensitizer with a solubility greater than that of MK, may be used as a sensitizer in any photochemically reactive solution that contains molecules having triplet energies of about or less than the triplet energy of EMK Also, metal halide-doped mercury arc lamps have not been used for solution-phase photochemical transformations other than for photopolymerizations. In particular, iron halide-doped mercury arc lamps had not previously been used for triplet sensitized [2+2] cyclizations exemplified by the norbornadiene to quadricyclane transformation.

From the above disclosure of the detailed description of the present invention and the preceding summary of the preferred embodiment, those persons skilled in the art will comprehend the various modifications to which the present invention is susceptible. Therefore, we desire to be limited only by the scope of the following claims and equivalents thereof.

We claim:

1. A process of driving a non-polymerization solution-phase photochemical transformation, comprising the steps of:
   providing an organic solution having the potential for a non-polymerization solution-phase photochemical transformation; and
   irradiating said organic solution with a metal-halide doped mercury arc lamp to drive said non-polymerization solution-phase photochemical transformation within said organic solution.

2. The process of claim 1 wherein said irradiating step is carried out with an iron halide-doped mercury arc lamp having an enhanced output in the range of about 340 nm to about 390 nm.

3. A process of driving a non-polymerization solution-phase photochemical transformation, comprising the steps of:
   providing a solution containing molecules having triplet energies up to about the triplet energy of a diaminobenzophenone sensitizer with a solubility in said solution greater than the solubility of Michler's Ketone;
   adding a diaminobenzophenone sensitizer to said solution, wherein said sensitizer has a solubility in said solution greater than Michler's Ketone; and
   irradiating said solution with light, said solution having said sensitizer added thereto, to drive a non-polymerization solution phase photochemical transformation within said solution.

4. The process of claim 3 wherein said sensitizer is Ethyl Michler's Ketone.

5. The process of claim 3 wherein said irradiating step is carried out with a metal halide-doped mercury arc lamp.

6. The process of claim 5 wherein said irradiating step is carried out with an iron halide-doped mercury arc lamp having an enhanced output in the range of about 340 nm to about 390 nm.

7. A process of driving a non-polymerization solution phase photochemical transformation, comprising the steps of:
   providing an organic solution having the potential for a non-polymerization solution-phase photochemical transformation;
   adding a base to said organic solution; and
   irradiating said organic solution with light, whereby said base reduces the formation of by-products during said non-polymerization solution phase photochemical transformation.

8. A process of driving a non-polymerization solution phase photochemical transformation, comprising the steps of:
   providing a solution having the potential for a non-polymerization solution-phase photochemical transformation;
   adding triethylamine to said solution; and
   irradiating said solution with light, whereby said triethylamine reduces the formation of by-products during said non-polymerization solution phase photochemical transformation.

* * * * *

UNITED STATES PATENT AND TRADEMARK OFFICE
CERTIFICATE OF CORRECTION

PATENT NO. : 6,635,152 B1
DATED : October 21, 2003
INVENTOR(S) : Paul A. Cahill et al.

It is certified that error appears in the above-identified patent and that said Letters Patent is hereby corrected as shown below:

Title page,
Item [56], References Cited, OTHER PUBLICATIONS, "Naman et al.", reference, "avaiable", should be -- available -- .

Column 3,
Line 1, "THE DRAWING" should be -- THE DRAWINGS --.
Lines 7,9, and 11, "norbornediene" should be -- norbornadiene --.
Line 20, "Norborhadiene" should be -- Norbornadiene --.
Line 53, "is" should be -- are --.

Column 5,
Line 26, "out put" should be -- output --.

Column 6,
Line 1, "were" should be -- was --.
Lines 15-18, "Norbornadiene to ..." should read -- More specifically, Fig. 2 illustrates norbornadiene to... --.

Figure 3:
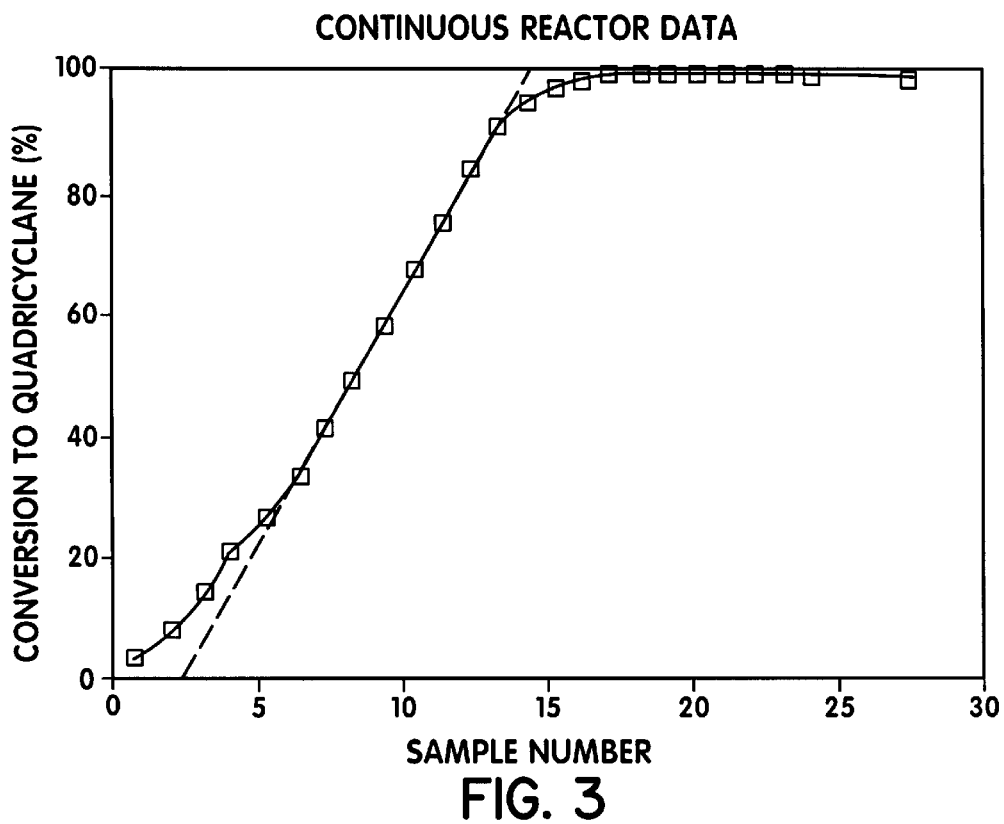
FIG. 3 shows the rate of conversion of norbornediene to quadricyclane, as measured by gas chromatography.

Column 7,
Lines 14-16, "Plot of conversion..." should read -- More specifically, Fig. 3 illustrates the plot of conversion... --.

Signed and Sealed this

Sixth Day of July, 2004

JON W. DUDAS
*Acting Director of the United States Patent and Trademark Office*